United States Patent [19]
Rogalsky

[11] Patent Number: 5,549,570
[45] Date of Patent: Aug. 27, 1996

[54] MEDICAL NEEDLE UNIT

[76] Inventor: Alena Rogalsky, 186 Pinehurst Ave., New York, N.Y. 10036

[21] Appl. No.: 235,642

[22] Filed: Apr. 29, 1994

Related U.S. Application Data

[63] Continuation-in-part of Ser. No. 9,983, Jan. 27, 1993, Pat. No. 5,425,720.

[51] Int. Cl.$^6$ ................................................ A61M 5/32
[52] U.S. Cl. .................................... 604/198; 604/192
[58] Field of Search ................................ 604/192, 110, 604/198

[56] References Cited

U.S. PATENT DOCUMENTS

| | | | |
|---|---|---|---|
| 4,863,435 | 9/1989 | Sturman et al. | 604/198 |
| 4,911,706 | 3/1990 | Levitz | 604/198 |
| 4,955,866 | 9/1990 | Corey | 604/198 |
| 5,015,242 | 5/1991 | Heifetz | 604/198 |
| 5,059,180 | 10/1991 | McLees | 604/198 |
| 5,059,184 | 10/1991 | Pyke | 604/198 |
| 5,368,568 | 11/1994 | Pitts et al. | 604/198 |

*Primary Examiner*—John G. Weiss
*Attorney, Agent, or Firm*—Ilya Zborovsky

[57] ABSTRACT

A medical needle unit has a needle having a tip insertable in as well as withdrawable from the body of a patient and a protective element for preventing accidental puncture by the tip of the needle after the withdrawal the tip of the needle from. The body, the protective element includes a hood moveable between an exposing position in which the tip of the needle is exposed and an enclosing position in which the tip of the needle is enclosed, a spring member connecting the hood with the needle so that when the spring member or members is compressed the hood is in the exposed position, and when the spring is relaxed the hood is in the enclosed position, and pivotal retaining element which in one position extends substantially parallel or perpendicular to the needle and retains the spring in the compressed position and therefore the hood in the exposed position before an injection by the needle and after the injection is pivotal to another position so as release the spring so that the spring relaxes and moves the hood to the enclosing position.

16 Claims, 3 Drawing Sheets

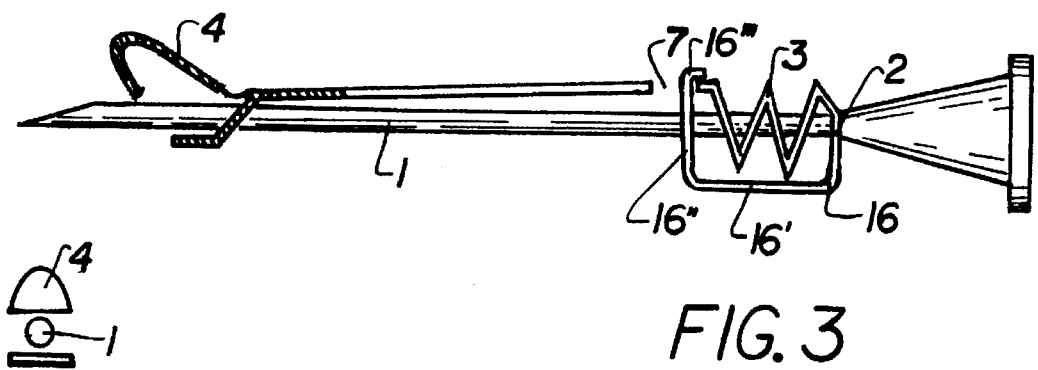
FIG. 3
FIG. 3'
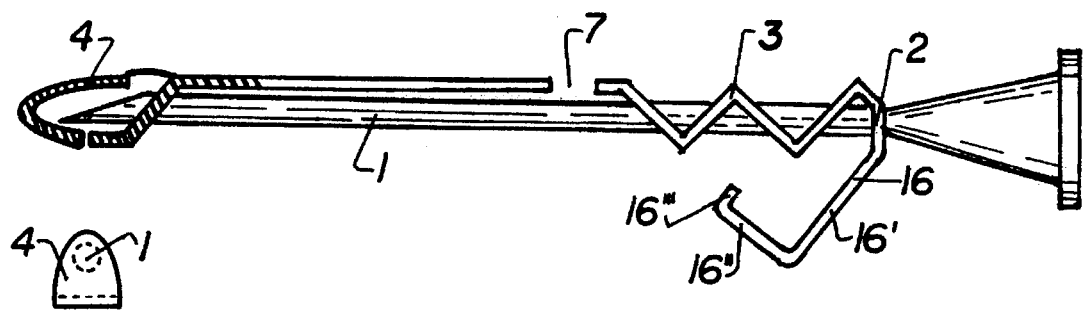
FIG. 4
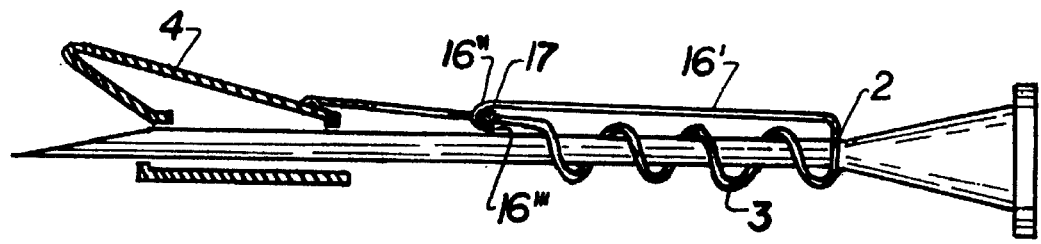
FIG. 5
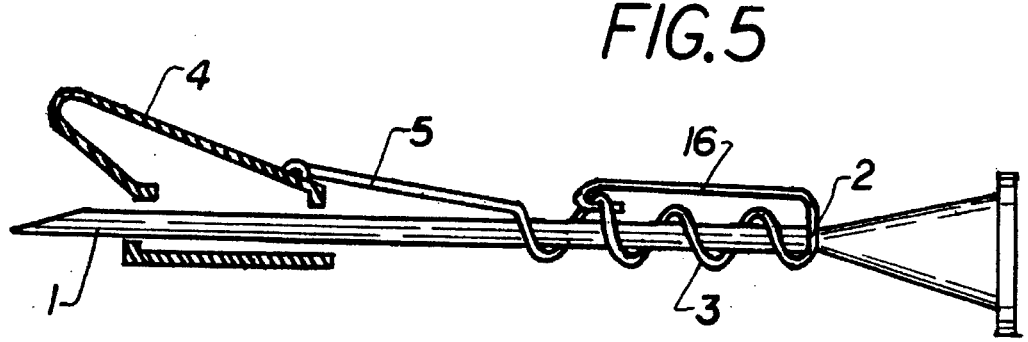
FIG. 5A

MEDICAL NEEDLE UNIT

CROSS-REFERENCE TO A RELATED APPLICATION

This application is a continuation in part of application Ser. No. 08/009,983 filed on Jan. 27, 1993, now U.S. Pat. No. 5,425,720.

BACKGROUND OF THE INVENTION

The present invention relates to medical needle units.

Medical needle units are widely known and used for injection and withdrawal of blood or other tissue fluids. After the withdrawal of blood or other tissue fluids, the needle of the needle unit is withdrawn from a muscle, vein, artery or another body area and a tip of the needle is exposed. The needle may be contaminated with microorganisms, and it is possible that a technician, nurse or physician can be accidentally punctured by the exposed needle tip. In the event of contamination of the needle with viruses, etc., it can lead to very serious or even grave consequences. It is to be understood that it is desirable to at least decrease the tendency of the operator to be accidentally struck by an exposed needle tip.

Several solutions have been proposed to avoid the accidental puncture. One of such solutions includes for example a cylindrical hood which is movably attached to the needle which moves first to an exposing position in which the tip of the needle is exposed before the injection and back to enclosing position in which the cylindrical hood encloses the tip of the needle after the injection. Another solution is a hood which moves along the syringe and is also displaced to cover the needle. It is believed that the existing solutions are quite complicated, not reliable, need additional procedures. It is therefore desirable to develop further protective elements for medical needle units which are simpler, less expensive, reliable and self-operating.

SUMMARY OF THE INVENTION

Accordingly, it is an object of the present invention to provide a medical needle unit which includes a needle and a protective element, which is an improvement of the existing protective elements.

In keeping with these objects and with others which will become apparent hereinafter, one feature of the present invention resides, briefly stated, in a medical needle unit which has a needle having a tip insertable in as well as withdrawable from the body of a patient and a protective element for preventing accidental puncture by the tip of the needle after the withdrawal of the tip of the needle from the body, the protective element including a hood moveable between an exposing position in which the tip of the needle is exposed and an enclosing position in which the tip of the needle is enclosed, a spring member connecting the hood with the needle so that when the spring member is compressed the hood is in the exposed position, and when the spring is relaxed the hood is in the enclosing position, and a pivotable retaining element which in one position extends substantially parallel to the needle and retains the spring in the compressed position and therefore the hood in the exposed position before an injection by the needle and after the injection is pivotable to another position which is not parallel to the needle so as to release the spring so that the spring relaxes and moves the hood to the enclosing position.

When the medical needle unit is designed in accordance with the present invention, it avoids the disadvantages of the prior art and provides for simple, self-operating and reliable protection from accidental puncture by a needle tip.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIGS. 3, 3' and 4, 4' are side and end views substantially corresponding to the views of FIGS. 1 and 2, but showing a further modification of the inventive medical needle unit, and FIG. 2" is a plan view of a fragment encircled in FIG. 2;

FIGS. 5 and 6 are views substantially corresponding to the views of FIGS. 1 and 2, but showing still a further modification of the inventive medical needle unit; FIG. 5' shows a plan view of a fragment encircled in FIG. 5; FIG. 5a shows still another modification of the medical needle unit.

FIGS. 9a, 9b and 9' are a plan view, a side view and an end view of the unit in accordance with the further embodiment of the invention, and FIGS. 10a and 10b are the same views of the same device after the injection.

DESCRIPTION OF THE PREFERRED EMBODIMENTS

Figure 1:
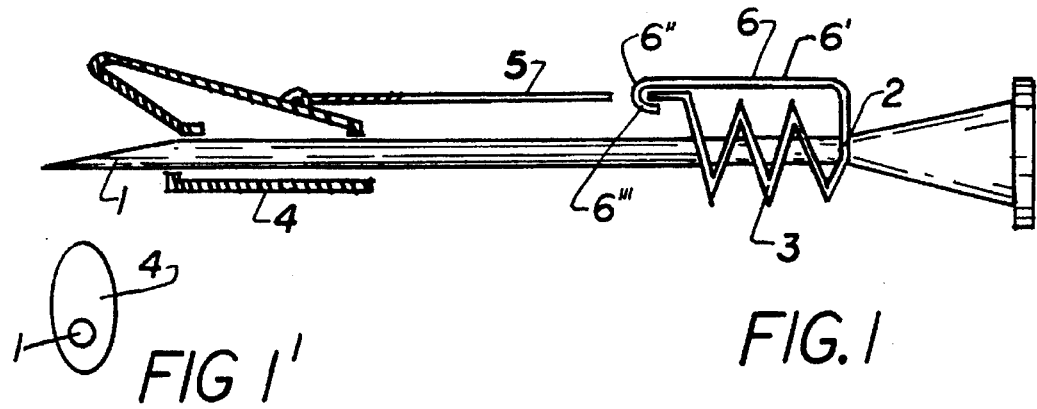
FIGS. 1, 1' and 2, 2' are side and end views showing a medical needle unit in accordance with the present invention before an injection and after the injection.
Figure 1A:
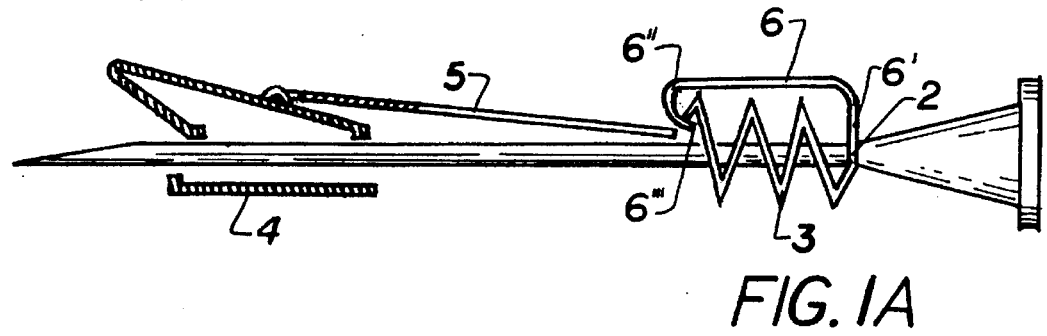
FIG. 1a shows another modification of the inventive medical needle unit.

A medical needle unit in accordance with a first embodiment of the present invention shown in FIGS. 1, 1' and 2, 2' has a needle which is identified with reference numeral 1 and has a front end with a tip and a rear end. The medical needle unit is provided with a protective element for preventing accidental punctures by the tip of the needle after withdrawal of the tip of the needle from the body and is identified with reference numeral 2. The protective element 2 includes a spring 3 which is connected with its rear end to a needle and is connected with its front end to a hood 4, for example through a connecting element 5. It is to be understood that the connecting element 5 can be just a part of the spring 3. The protective element is further provided for example with an opening 7 which is formed for example in the connecting element 5 as shown in FIG. 1, or with an opening 7' which is provided in the spring 3 as shown in FIG. 1a. The protective element further has a retaining element which is identified as pivotable whole with reference numeral 6 and has a first portion 6' extending substantially parallel to the needle 1 at one radial side of the needle, and a second portion 6" extending transversely to the first portion. The second portion 6" can end in a third portion 6'" which extends rearwardly from the second portion at an opposite radial side of the needle 1. As can be seen from the drawings, the second portion 6" extends across the needle 1. The second portion 6" can be fork-shaped so that the needle passes through an opening between the legs of the fork-shaped portion. The whole protective element 3, 4, 5, 6 can be made as a one-piece element composed of a synthetic plastic material or steel.

Figure 2:
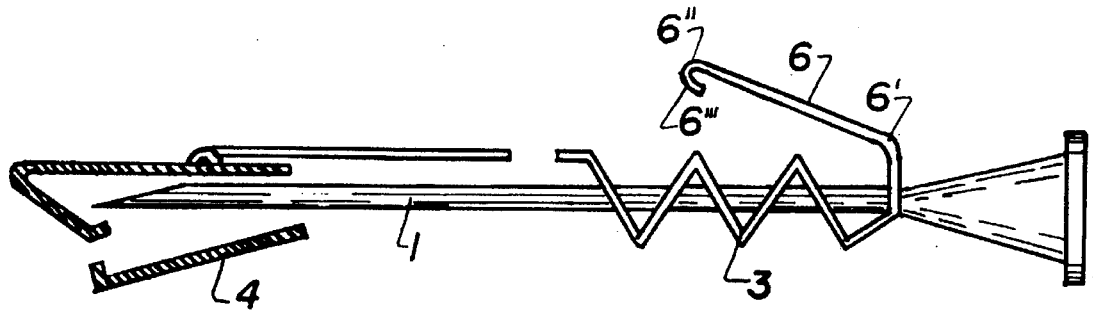
Figure 2:
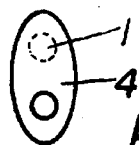

In the position shown in FIG. 1, the retaining element 6 engages in the opening 7 and retains the spring 3 in its compressed position, and therefore the hood 4 is retained in a position in which the tip of the needle is exposed. During the injection the hood 4 is moved rearwardly on the needle 1, the spring 3 is compressed, and the retaining element 6 pivots from its position in which it is parallel to the needle as shown in FIG. 1, to its position in which it is turned from its first position and its retaining end is disengaged from the opening 7 so as to release the spring. In order to obtain this effect, the spring and the connecting element must be prestressed so that in the position shown in FIG. 1 it is stressed, while in the position shown in FIG. 2 it is relaxed because they are made of elastic material. When the spring 3 is no longer retained by the retaining element 6, it is relaxed and pushes the hood 4 forwardly so that the hood completely encloses the tip of the needle to prevent accidental punctures by the tip of the needle after the injection.

In the embodiment of FIG. 1a the retaining element 6 engages with and disengages from the spring 3.

The embodiment shown in FIGS. 3, 3' and 4, 4' is substantially similar to the embodiment shown in FIGS. 1, 1' and therefore those parts of the second embodiment which are similar to the parts of the first embodiment are identified with the same reference numerals. In the second embodiment of FIGS. 3, 3' and 4, 4' the retaining element 16 is somewhat different. Its rear end is also connected to the needle (or to the fixed end of the spring). The retaining element has a first portion 16' which extends substantially parallel to the needle 1 at one radial side of the needle, a second portion 16" which extends transversely to the first portion, and a short third portion 16''' which extends from the second portion back and also substantially parallel to the needle. The retaining element of FIGS. 3, 3' and 4, 4' differs from the retaining element of FIGS. 1 and 2 in that the retaining element as a whole, including the portions 16', 16", and 16''', is located only at one radial side of the needle 1. It does not have any portions extending transversely across the needle and therefore it does not have to be fork-shaped or have an opening for passing the needle.

Figure 6:
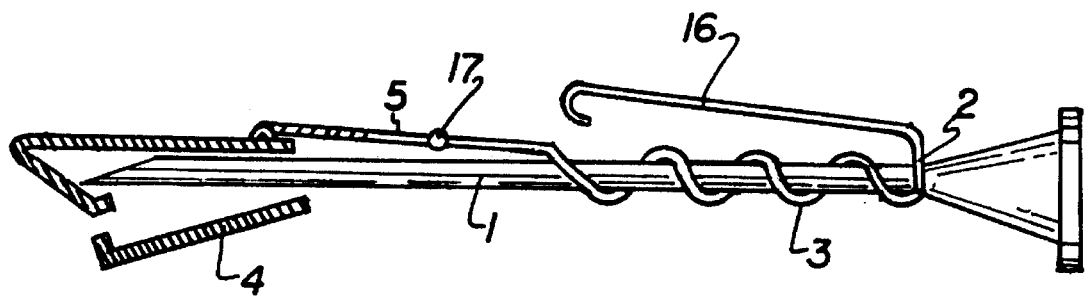

The medical needle unit in accordance with the third embodiment shown in FIGS. 5 and 6 substantially corresponds to the medical unit of the first two embodiments, therefore the parts of the third embodiment which are similar to the parts of the previous embodiments are identified with the same reference numerals. In the third embodiment the protective element is provided with a thickening 17 which can be arranged for example on a connecting part 5 or on a spring 3' and can be formed for example as a ball, a roller or the like. In the position before the injection, the retaining element 16 engages the thickening 17 and retains the spring in its compressed position. During the injection the retaining element 16 releases the thickening 17, and the spring 3' relaxes pushing the hood 4 forwardly so as to completely enclose the tip of the needle 1. The second and third portions 16" and 16''' of the retaining element 16 are fork-shaped so that the connecting part 5 can pass in an opening between the legs of the retaining element, but the distance between the legs is smaller than the width of the thickening 17 so as to provide engagement of the free end of the retaining element with the thickening.

In the embodiment of FIG. 5a the retaining element 16 engages with and disengages from a convolution of the spring.

Figure 7:
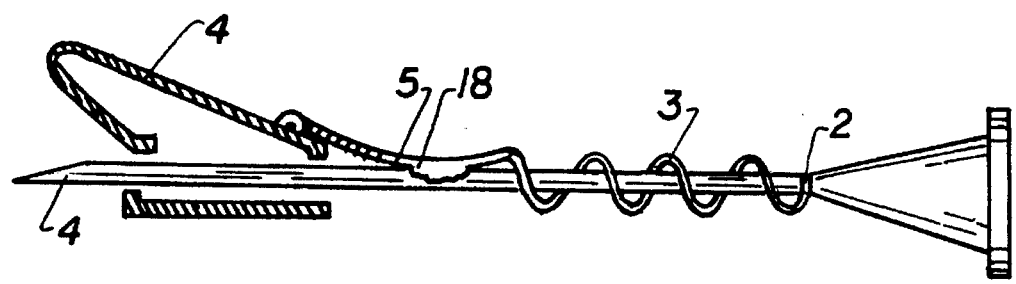
FIGS. 7 and 8 are views substantially corresponding to the views of FIGS. 1 and 2 and showing still another embodiment of the invention.
Figure 8:
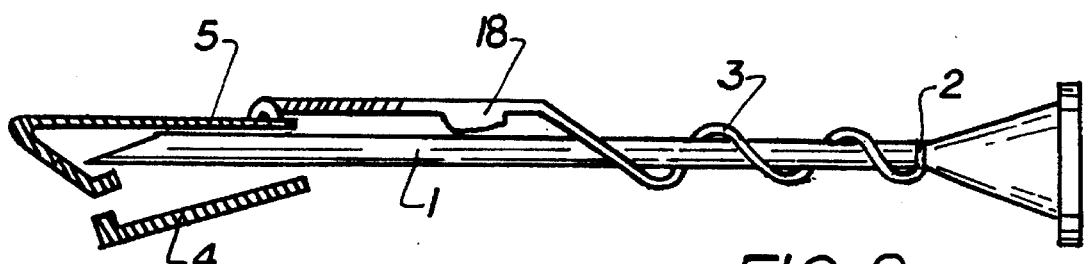

FIGS. 7 and 8 show a further embodiment of the inventive needle unit. In this embodiment the parts similar to the previous embodiments are identified with the same reference numerals. Here, the spring 3 or the connecting element 5 is temporarily connected directly to the needle for example in a point as identified with reference numeral 18. The connection 18 can be made for example by welding if the materials of the spring and connecting element on the one hand and of the needle on the other hand are weldable together. If these materials are plastic materials they can be easily welded. If one of the materials is plastic and another of the materials is metal, the plastic can be melted to adhere to the metal. If both materials are metals they can be connected by welding or soldering, etc. During the injection the hood 4 or the connecting element 5 displaces rearwardly and its rear end removes the connection 18 and releases the spring 3 so that after the injection the spring 3 pushes the hood 4 forwardly and the hood assumes its enclosing position.

FIGS. 9a, 9b, 10a,10b are views showing a unit in accordance with a further embodiment which is especially suitable for butterfly-type needles. The retaining element 16 has one end pivotally connected with the butterfly part of the needle and another end provided with a hook which before the injection engages with an opening in the hood 4 and retains the spring 3 in its retracted position and also retains the hood in the same position. After the injection the hook on the end of the of the retaining element 16 disengages from the hood 4 and pivots sideways under the action of its pre tensioning. The spring 3 is thereby released and pushes the hood 4 forwards so that the latter closes tip of the needle.

It will be understood that each of the elements described above, or two or all together, may also find a useful application in other types of constructions differing from the types described above.

While the invention has been illustrated and described as embodied in a medical needle unit, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A medical needle unit, comprising a needle having a tip insertable in as well as withdrawable from the body of a patient and a protective element for preventing accidental puncture by said tip of said needle after the withdrawal of said tip of said needle from the body, said protective element including a hood moveable between an exposing position in which said tip of said needle is exposed and an enclosing position in which said tip of said needle is enclosed, a spring member connecting said hood with said needle so that when the spring member is compressed said hood is in said exposed position, and when said spring is relaxed said hood is in said enclosing position, a connecting element which connects said hood with said spring member, and a pivotable retaining element which in one position extends substantially parallel to said needle and retains said spring in said compressed position and therefore said hood in said exposed position before an injection by said needle and after the injection is pivotable to another position which is not parallel to said needle so as to release said spring so that said spring relaxes and moves said hood to said enclosing position, said hood, said spring member, said connecting element, and said retaining element of said protective element being formed so that during injection said hood is displaced toward a needle end to expose said tip of said needle and automatically without being actuated by a user, and after withdrawal of said needle from a patient said hood moves toward said tip also automatically without being actuated by a user.

2. A medical needle unit as defined in claim 1, wherein said retaining element has one end pivotally connected with said needle and another end engaging said spring so as to retain it in said compressed position and disengaging from said spring member so as to release said spring member.

3. A medical needle unit as defined in claim 2, wherein said retaining element has a first portion extending from said one end substantially parallel to said needle and a second portion provided at said another end and extending transversely to said first portion and forming said another end.

4. A medical needle unit as defined in claim 3, wherein said first portion of said retaining element extends at one radial side of said needle, said second portion of said retaining element extends from said first portion transversely to said needle to another radial side of said needle and engages said spring member at said another side of said needle.

5. A medical needle unit as defined in claim 3, wherein said first portion of said retaining element extends at one radial side of said needle, said second portion extends transversely to said first portion and engages said spring member at said one radial side of said needle.

6. A medical needle unit as defined in claim 3, wherein said second portion of said retaining element is fork-shaped.

7. A medical needle unit as defined in claim 2, wherein said spring member has an opening, said another end of said retaining element being engageable in said opening and disengageable from said opening.

8. A medical needle as defined in claim 2, wherein said spring member has a thickening, said another end of said retaining element being engageable with said thickening and disengageable from said thickening.

9. A medical needle as defined in claim 8, wherein said another end of said retaining element is fork-shaped.

10. A medical needle unit as defined in claim 1, wherein said spring member has flat convolutions.

11. A medical needle unit as defined in claim 1, wherein said spring member has round convolutions.

12. A medical needle unit as defined in claim 1, wherein said retaining element is engageable with and disengageable from a convolution of said spring member.

13. A medical needle unit as defined in claim 1, wherein said connecting element has an opening, said retaining element having a free end engageable in said opening before an injection and disengageable from the same after the injection to allows said spring to push said hood to said enclosing position.

14. A medical needle unit, comprising a needle having a tip insertable as well as withdrawable from the body of a patient and a protective element for preventing accidental puncture by said tip of said needle after the withdrawal of said tip of said needle from the body, said protective element including a hood movable between an exposing position in which said tip of said needle is exposed and an enclosing position in which said tip of said needle is enclosed, a spring member connecting said hood with said needle so that when said spring member is compressed said hood is in said exposed position and when said spring member is relaxed said hood is in said enclosed position, and a retaining element which forms a connection which connects said spring with said needle and therefore retains said spring in said compressed position and said hood in said exposing position before an injection by said needle, said hood and said connection being formed so that during the injection said hood displaces toward said connection and releases said retaining element so as to release said spring and to relax said spring so that said spring moves said hood to said enclosing position.

15. A medical needle unit as defined in claim 14, wherein said connection is a weld seam connection.

16. A medical needle unit as defined in claim 14, wherein said connection is a solder seam connection.

* * * * *